(12) United States Patent
Wilson et al.

(10) Patent No.: US 8,148,562 B2
(45) Date of Patent: Apr. 3, 2012

(54) SUBSTITUTED ORGANOPOLYSILOXANES AND USE THEREOF

(75) Inventors: John Robert Howe Wilson, London (GB); Alice Caroline Sullivan, London (GB); Siud Pui Man, Oxford (GB)

(73) Assignee: PhosphonicS Ltd, Oxford (GB)

( * ) Notice: Subject to any disclaimer, the term of this patent is extended or adjusted under 35 U.S.C. 154(b) by 684 days.

(21) Appl. No.: 11/659,330

(22) PCT Filed: Jul. 28, 2005

(86) PCT No.: PCT/EP2005/008326
§ 371 (c)(1),
(2), (4) Date: Oct. 28, 2008

(87) PCT Pub. No.: WO2006/013080
PCT Pub. Date: Feb. 9, 2006

(65) Prior Publication Data
US 2009/0062234 A1 Mar. 5, 2009

(30) Foreign Application Priority Data
Aug. 4, 2004 (GB) .................................. 0417344.9

(51) Int. Cl.
C07F 7/18 (2006.01)
A61K 31/695 (2006.01)
A01N 55/00 (2006.01)
(52) U.S. Cl. .............. 556/9; 556/51; 556/138; 556/136; 556/440; 556/482; 514/63
(58) Field of Classification Search .................. None
See application file for complete search history.

(56) References Cited

U.S. PATENT DOCUMENTS

| | | | | |
|---|---|---|---|---|
| 2,605,243 A | * | 7/1952 | Sowa | 525/445 |
| 6,140,445 A | * | 10/2000 | Su et al. | 528/15 |
| 6,395,856 B1 | * | 5/2002 | Petty et al. | 528/24 |
| 6,756,217 B1 | * | 6/2004 | Dave et al. | 435/176 |

OTHER PUBLICATIONS

Marciniec et al., {Catalysis of hydrosilylation. XXIII. Effect of substituents at silicon on unusual hydrosilylation of vinylsilanes catalyzed by nickel acetylacetonate, Journal of Organometallic Chemistry (1993), 454(1-2), 45-50}.*

Benati et al., {A novel tin-free procedure for alkyl radical reactions, Angewandte Chemie, International Edition (2004), 43(27), 3598-3601}.*

Smith et al., {Bond refractions in organosilicon compounds. I, Svensk Kemisk Tidskrift (1949), 61, 213-17}.*

* cited by examiner

Primary Examiner — Yate K Cutliff
(74) Attorney, Agent, or Firm — Oblon, Spivak, McClelland, Maier & Neustadt, L.L.P.

(57) ABSTRACT

The present invention provides a compound of Formula 1:

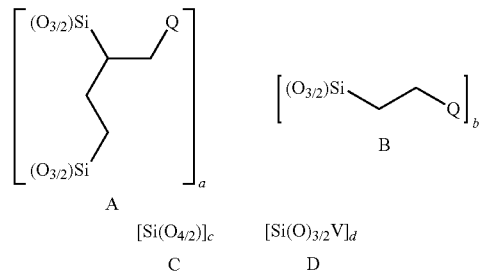

The compound of Formula 1 is useful as a scavenger for the removal of unwanted organic and inorganic compounds, for solid phase extraction, for solid phase synthesis, for the immobilization of bio-molecules, as ion exchanger materials, as catalysts and catalyst supports and as chromatography materials.

21 Claims, No Drawings

SUBSTITUTED ORGANOPOLYSILOXANES AND USE THEREOF

The invention relates to new organopolysiloxanes and their use, for example as catalysts, cation and anion exchangers, organic and inorganic compound scavengers, solid phase purification or extraction materials, immobilisation materials for bio-molecules, anti-microbial agents, hydrophilicity modifiers, flameproofing agents, antistatic agents, biomedical devices, water repellent films and coatings, solid phase synthesis materials and chromatography materials. The invention also relates to precursors of these new products and processes for their production.

The use of functionalised solids is growing rapidly for many different applications such as solution phase synthesis, solid phase synthesis, solid phase extraction, catalysis, catalyst supports, product purification and the immobilisation of bio-molecules. In these applications the advantages of functionalised solids are ease of manipulation, simple separation from the rest of the medium by filtration and regeneration and reuse. Key requirements for these functionalised solids are excellent physical and chemical stability over a wide range of operating conditions, broad solvent applicability, fast kinetics—fast and easy access to the functional groups and functional groups with high intrinsic activity for the desired application. In addition the preparation of these functionalised materials has to be simple from readily available reagents. Finally it is highly advantageous if the functional groups can be readily transformed into different functionalised materials that can be used for other applications.

Substituted polystyrene derivatives are an important class of materials being used for a range of applications. The chemical and physical properties of a variety of such polystyrene based systems are described in the Bio-Rad Life Science Research Products catalogue 1998/99, pages 56-64. However the physical and chemical properties of these polystyrene resins may possess disadvantages, for example poor chemical stability and thermal stability, believed to be due to the organic polymeric backbone. Additional problems for example swelling and shrinking in organic solvents as well as the production of highly coloured unwanted side products may also be encountered. Generally, due to their poor thermal stability, these polystyrene resins cannot be used for any length of time above 80° C., thus limiting their general applicability. In addition a range of chemical functionality cannot be readily attached to these organic polymers due to the physical limitations of these polymers and the range of chemistry that can be used to attaché functional groups onto the aromatic rings.

Inorganic polymer systems such as silica, aluminium oxide and titanium oxide have also been disclosed as functionalised materials. Active functional groups or metals can be attached by a variety of means to these systems. However a number of problems may be encountered where the functional groups are only physically adsorbed for example low functional group loading along with limitations in the range of solvents that can be used and removal of the functional groups on use or on standing. This is believed to be due to the rather weak attachment between the functional group and the surface atoms on the support. Building the functional group into the framework may provide a more robust material and may also permit higher functional group loadings. However in this approach there is a significant lack of readily available starting materials as well as precursors for preparing such starting materials. In addition there are limited synthetic methodologies for the preparation of suitable starting materials from available precursors. A need exists to provide new synthetic methods as well as starting compounds in order to make such functionalised materials.

In solution phase organic synthesis functionalised solid materials are used to aid rapid purification and workup. Here these functionalised solid materials, also known as scavengers, can remove excess reagents and side products. At the end of the reaction the scavenger is added to quench and selectively react with excess or unreacted reagents and reaction side products. The unwanted chemicals now attached to the functionalised materials are removed by simple filtration. This simple process circumvents the standard purification methodologies of liquid-liquid extraction, chromatography and crystallisation. Substituted polystyrene derivatives are the main class of materials being used as scavengers. However as described above these materials suffer a number of significant limitations such as lack of thermal stability (stable up to 80° C.), swelling and shrinking in organic solvents and a limited range of functional groups. In addition to the need to remove unwanted chemicals from the desired product there is a requirement to separate closely related compounds. For example the separation of primary amines from secondary or secondary amines from tertiary amines is a particular requirement in both the fine chemical and pharmaceutical industries.

In solid phase synthesis substituted polystyrene derivatives are the main class of materials being used and likewise these materials suffer the same limitations as described above. The use of functionalised silica materials for this application is limited by the availability of suitable functionalised materials.

Catalysts are utilised in the chemical and biochemical industry to conduct a wide range of chemical transformations. A range of homogenous and heterogeneous catalysts are used some of which require high temperatures to be effective and some produce considerable amount of bi-products and waste. These unwanted products and waste have to be treated and destroyed. The drive for more environmentally friendly processes—Green Chemistry—highlights the need for reusable, more effective and selective catalysts. Examples of catalysts currently used extensively across manufacturing industries include mineral acids—sulphuric acid, hydrochloric acid, hydrogen fluoride, phosphoric acid—Lewis acids—aluminium trichloride, boron trifluoride and zinc chloride—and oxidation reagents—permanganate, manganese dioxide and chromium (VI). Catalysts, particularly solid phase catalysts, suitably have one or more of the following characteristics; good thermal stability, good chemical stability, flexibility to tailor the loading of functional groups to optimise yield and selectivity, they do not swell to a material extent, ease of regeneration and good catalyst life. This need has led to investigations into the design of new materials that can either catalyse a variety of chemical transformations or be used as a catalyst solid support. In the latter the catalysts are firmly attached onto functional groups that are strongly attached onto a stable support.

Key requirements for such new catalysts and catalyst supports are very good thermal stability, high insensitivity to chemical attack, high functional group loading, fixed and rigid structures, optimum functional groups so as to avoid rearrangements and side products, limited swelling capability, insolubility in organic solvents, ease of purification and high reusability, high ageing resistance and ease of access to the functional group which conducts the chemical transformation. In addition the processes to make such catalyst systems and catalyst supports have to be flexible so as to enable the production of optimum structures and shapes for specific reactions. This could include tailoring the porosity from anywhere between macroporous to microporous structures, variable loading of the functional group, ease of making different metal derivatives and selective pH ranges. Of particular interest for new catalysts and catalyst supports are functional groups such as carbonyl and carboxy due to their ease of manipulation and their capabilities to bind to metal complexes.

A range of metals and catalysts have been embedded within or adsorbed on to the surface of silica, and other materials These systems may suffer the drawback of loss of the active functional groups due to their often very weak attachment to the silica. A need remains for organo-silica materials which whilst retaining the appropriate function have functional groups that are strongly attached to the support and which bind strongly to a range of metals and catalysts and do not catalyse other reactions to an undesirable extent which may lead to impure and highly coloured products and lower yield and selectivity.

As a consequence of stricter environmental regulations there is a growing requirement for more effective systems for the removal and recovery of cations and anions from many sources including a wide spectrum of contaminated solvents and aqueous based wastes and from contaminated waters. For example the electronics industry has a particular need for ultra pure water with very low levels of both cations and anions. Other industries such as the nuclear industry and the electroplating industry generate substantial quantities of water-based effluent that are heavily contaminated with undesirable metal ions. Cation exchangers have been used to remove metal ions from solution. Polymers having an organic partly cross-linked polystyrene backbone with sulfonate groups attached to some of the phenyl rings are known for use in this application and have certain drawbacks as regards physical and chemical properties of these polystyrene sulfonic cation exchangers are strongly affected by the organic nature of the polymeric backbone so that a number of disadvantages affect their technical field of application as noted above. The type of cation exchangers employed, consist primarily of an organic, partly cross-linked polystyrene backbone with sulfonate groups attached to some of the phenyl rings. The physical and chemical properties of these polystyrene sulfonic cation exchangers are strongly affected by the organic nature of the polymeric backbone so that a number of disadvantages affect their technical field of application. Organophosphonic acid cation exchangers have also been reported in U.S. Pat. No. 5,281,631 and U.S. Pat. No. 5,449,462. The feedstock in the manufacture of these materials may be expensive and they have limited applicability due to their physical and chemical properties.

The invention relates to novel compounds which have a wide range of uses including acting as scavengers for inorganic and organic compounds, solid phase extraction and purification material, bio-molecule immobilisation supports, ion exchanger materials, as anti-microbial agents and as chromatography materials, as catalysts and catalyst supports or which are precursors for these.

In a first aspect of the present invention, there is provided a compound of General Formula 1:

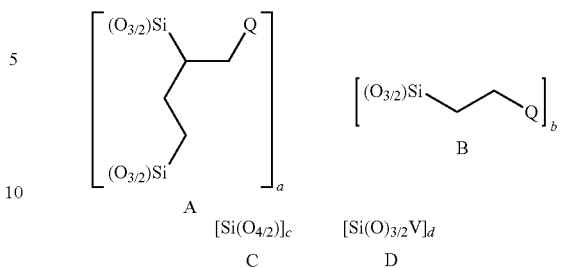

Formula 1 wherein Q is selected from $CXYR^1$ and $—C(Z)R$ wherein Z is selected from oxygen, hydrogen, OH, $NR^2$ and $NNR^2R^3$, and wherein X and Y are each selected from hydrogen, $—C(Z)R$, CN or C(O)W and W is selected from OH, $OR^6$, $O(M^{+n})_{1/n}$, and $NR^2R^3$ and R, $R^1$, $R^2$, $R^3$ and $R^6$ are each selected from hydrogen, an optionally substituted linear or branched group selected from $C_{1-40}$-alkyl, $C_{2-40}$-alkenyl, $C_{2-40}$-40-alkynyl group, an aryl and $C_{1-40}$-alkylaryl group and M is a metal ion derived from a lanthanide, actinide, main group or transition metal and V is selected from an optionally substituted linear or branched group selected from $C_{1-40}$-alkyl, $C_{2-40}$-alkenyl, $C_{2-40}$-alkynyl group, an aryl group, a $C_{1-40}$-alkylaryl, sulfide, sulfoxide, sulfone, amine, a polyalkyl amine, a phosphine or other phosphorous containing group; n is an integer from 1 to 4;

the free valences of the silicate oxygen atoms are saturated by one or more of:

silicon atoms of other groups of Formula 1, hydrogen, a linear or branched $C_{1-12}$-alkyl group, by end groups $R^4_3M^1O_{1/2}$, by cross-linking bridge members $R^4_qM^1(OR^5)_mO_{k/2}$, $Al(OR^5)_{3-p}O_{p/2}$ or $R^4Al(OR^5)_{2-r}O_{r/2}$ or by chains, for example polymeric chains, comprising $(R^4_eSiO_{f/2})_g$;

where $M^1$ is Si or Ti; e is an integer from 2 to 3 and f is an integer from 1 to 2 such that e+f=4 and g is an integer from 1 to $10^8$, preferably from 1 to 100;

$R^5$ is a linear or branched $C_{1-40}$, preferably $C_{1-12}$-alkyl group, an aryl or $C_{1-40}$-alkylaryl group; and $R^4$ is a linear or branched $C_{1-40}$-alkyl group, an aryl or $C_{1-40}$-alkylaryl group;

k is an integer from 1 to 3 and q and m are integers from 0 to 2;

such that m+k+q=4;

p is an integer from 1 to 3; and r is an integer from 1 to 2;

or other known oxo metal bridging systems where the metal is zirconium, boron, magnesium, iron, nickel or one of the lanthanides; wherein both B and C are always present and the integers a, b, c and d are such that the ratio of b:a+c+d is from 0.00001 to 100,000.

Where a cross linker or polymer chain is used, it is preferred that the ratio of end groups and/or cross linker and/or polymer chains to a+b+c+d varies from 0 to 999:1 and preferably 0.001 to 999:1.

General Formula 1 may be abbreviated to $A_aB_bC_cD_d$ where A represents $[O_{3/2}SiCH(CH_2Q))CH_2CH_2SiO_{3/2}]$, B represents $[O_{3/2}SiCH_2CH_2Q]$, C represents $[O_{4/2}Si]$ and D represents $[O_{3/2}SiV]$.

One advantage of compounds of Formula 1 is that the functional group or groups can be selected to have either a high or low value according to the application. Compounds of Formula 1 are advantageous in a number of applications including as catalysts, catalyst immobilisation supports, organic compound scavengers, solid phase purification and extraction material, bio-molecule immobilisation supports, cation and anion exchanger materials, anti-microbial agents and chromatography materials. Other advantages include high thermal stability, fixed and rigid structures, good stability to a wide range of chemical conditions, insolubility in organic solvents, high resistance to ageing, easily purified and high reusability. In addition the processes for the preparation of compounds of Formula 1 are very flexible, enabling porosity to be tailored from micro to macro porous, the loading of the functional groups X and Y as well as the other substituents in the fragment V to be varied as needed for example to provide high loading of functional groups if required and a wide range of metal derivatives to be made with the added advantage of a high metal incorporation.

The organic groups R, $R^1$, $R^2$, $R^3$, $R^4$, $R^5$ and $R^6$ may independently be substituted with one or more substituents but preferably contain only hydrogen and carbon atoms. If a substituent is present, it may be selected from nitro, chloro, fluoro, bromo, nitrile, hydroxyl, carboxylic acid carboxylic esters, sulfides, sulfoxides, sulfones, $C_{1-6}$-alkoxy, a $C_{1-40}$-alkyl or aryl di substituted phosphine, amino, amino $C_{1-40}$-alkyl or amino di($C_{1-40}$-alkyl) or $C_{1-40}$-alkyl phosphinic or phosphonic group. The organic groups R, $R^1$, $R^2$, $R^3$, $R^4$, $R^5$ and $R^6$ may, independently be linear or branched as desired.

Each organic group R, $R^1$, $R^2$, $R^3$, $R^4$, $R^5$ and $R^6$ is selected independently of any of the other organic groups in the compound of Formula 1. Preferably, the organic groups R, $R^1$, $R^2$, $R^3$, $R^4$, $R^5$ and $R^6$ are independently selected from linear or branched $C_{1-22}$ and desirably $C_{1-12}$ alkyl, $C_{2-22}$- and desirably $C_{2-12}$ alkenyl, aryl and a $C_{1-22}$-alkylaryl group and especially preferred that the organic group R, $R^1$, $R^2$, $R^3$, $R^4$, $R^5$ and $R^6$ are independently selected from a linear or branched $C_{1-8}$ alkyl, $C_{2-8}$-alkenyl, aryl and a $C_{1-8}$-alkylaryl group.

Suitably, R, $R^1$, $R^2$, $R^3$, $R^4$, $R^5$ and $R^6$ are independently a $C_{1-12}$-alkyl group for example methyl or ethyl, or a phenyl group. Preferably q is from 1 to 2, k is from 1 to 3 and m is 0 provided that m+k+q=4.

Examples of suitable alkyl groups include methyl, ethyl, isopropyl, n-propyl, butyl, tert-butyl, n-hexyl, n-decyl, n-dodecyl, cyclohexyl, octyl, iso-octyl, hexadecyl, octadecyl, iso-octadecyl and docosyl. Examples of suitable alkenyl groups include ethenyl, 2-propenyl, cyclohexenyl, octenyl, iso-octenyl, hexadecenyl, octadecenyl, iso-octadecenyl and docosenyl.

$C_{1-6}$-alkoxy refers to a straight or branched hydrocarbon chain having from one to six carbon atoms and attached to an oxygen atom. Examples include methoxy, ethoxy, propoxy, tert-butoxy and n-butoxy.

The term aryl refers to a five or six membered cyclic, 8-10 membered bicyclic or 10-13 membered tricyclic group with aromatic character and includes systems which contain one or more heteroatoms, for example, N, O or S. Examples of suitable aryl groups include phenyl, pyridinyl and furanyl. Where the term "alkylaryl" is employed herein, the immediately preceding carbon atom range refers to the alkyl substituent only and does not include any aryl carbon atoms. Examples of suitable alkaryl groups include benzyl, phenylethyl and pyridylmethyl.

Compounds in which Q is —C(Z)R and Z is selected from oxygen, OH, hydrogen, $NR^2$ and $NNR^2R^3$ and R is $C_{1-12}$-alkyl, preferably $C_{4-12}$-alkyl, phenyl or $C_{1-8}$-alkylaryl and V is vinyl, $C_{1-4}$-alkyl, phenyl or $C_{1-8}$-alkylaryl are especially preferred.

Compounds in which Q is $CXYR^1$ wherein X and Y are each independently hydrogen, —C(Z)R, CN or C(O)W, Z is selected from oxygen, OH, hydrogen, $NR^2$ and $NNR^2R^3$ and W is selected from OH, $OR^6$, $O(M^{+n})_{1/n}$ and $NR^2R^3$ and R, $R^1$, $R^2$, $R^3$ and $R^6$ are each independently hydrogen, an optionally substituted linear or branched $C_{1-8}$-alkyl, $C_{2-8}$-alkenyl, $C_{2-8}$-alkynyl group, an aryl or $C_{1-12}$-alkylaryl group and M is a metal ion derived from a lanthanide, actinide, main group or transition metal and n is an integer from 1 to 4; and V is vinyl, $C_{1-4}$-alkyl, phenyl or $C_{1-4}$-alkylaryl are also especially preferred.

Group Z may be either a divalent species for example a carbonyl oxygen or may comprise two monovalent species together, for example H and OH.

Where a cross linker is used, it is preferred that the ratio of cross linker or polymer chains to a+b+c+d varies from 0 to 99:1 and preferably 0.01 to 99:1. Particularly suitable cross linkers, end groups or polymer chains are derived from titanium alkoxides, aluminium trialkoxides and alkyl alkoxy silanes. Examples of cross linkers include aluminium triethoxide, aluminium tributoxide and titanium isopropoxide and for polymer chains alkyl alkoxy silanes. The end group, cross linking bridge or polymer chain member is preferably $(R^4)_3SiO_{1/2}$ or $(R^4)_2SiO_{2/2}$ or $TiO_{4/2}$ or $R^4TiO_{3/2}$ or $(R^4)_2TiO_{2/2}$ or $AlO_{3/2}$ or $R^4AlO_{2/2}$. $R^4$ is preferably $C_{1-4}$-alkyl or aryl, most preferably methyl or ethyl or phenyl.

The preparation of compounds of Formula 1 will now be discussed in greater detail. The general procedure used for the production of the organopolysiloxanes of Formula 1 consists of first forming the compounds $(R^5O)_3SiCH_2CH_2Q$ or $(R^5O)_3SiCH(CH_2Q)CH_2CH_2Si(OR^5)_3$ and $(R^5O)_3SiCH_2CH_2Q$, and then combining them with tetraalkyl orthosilicate, $(R^5O)_4Si$, alone or with other compounds such as $(R^5O)_3SiV$, titanium alkoxides, aluminium trialkoxides and alkyl alkoxy silanes, in the desired ratios, in solvent with either dilute acid or base. An alternative method for the preparation of compounds of Formula 1 involves the treatment of preformed materials such as silica or aluminium oxide with $(R^5O)_3SiCH_2CH_2Q$ or $(R^5O)_3SiCH(CH_2Q)CH_2CH_2Si(OR^5)_3$ and $(R^5O)_3SiCH_2CH_2Q$ to give the corresponding functionalised material.

Organopolysiloxanes of Formula 1 where X or Y or both X and Y contain one or more carbonyl groups can be transformed into other materials of Formula 1 containing either alcohol, amide or imine functional groups via reduction or through reaction with an amine or hydrazine.

It has been reported that substituted ketones, esters and nitriles can be prepared through the free radical addition of aldehydes, esters or nirtiles to double bonds. This is described in *Org. Reactions*. Vol. 13, 108. The majority of this work concerns the addition of aldehydes or esters to simply substituted olefins. Emphasis was primarily on unsubstituted $C_{2-16}$ olefins. For silicon containing olefins there are only a small number of examples that include the reaction of butanal with trimethyl vinylsilane reported in *J. Amer. Chem. Soc.*, 1954, 76, 1615 to give 1-(trimethylsilyl) hexan-3-one using benzoyl peroxide as the free radical generator. Photochemical addition of aldehydes to vinyl silanes has been reported in Bull. Acad. Sci. USSR Div. Chem. Science 1966, 1405 to give the corresponding ketone $(RO)_3SiCH_2CH_2COR$ where R is methyl, propyl and phenyl. Aqueous acid hydrolysis of $(EtO)_3SiCH_2CH_2COCH_3$ gave a soft polymer of formula $[CH_3COCH_2CH_2SiO_{3/2}]_n$, that doesn't have the required physical properties for use as a solid material.

It is known that free radical reactions involving alkenes may not proceed in high yield or selectivity, depending on the particular starting materials unwanted dimers and higher tellomers may undesirably be produced, as disclosed in *Org. Reactions*, Vol. 13, page 218-222 and the references provided therein. However there is a lack of simple and effective synthetic methodology for the preparation of functionalised organic or inorganic polymers or materials. Furthermore there is a significant lack of readily available starting materials as well as precursors for preparing such starting materials. In addition there are limited synthetic methodologies for the preparation of suitable starting materials from available precursors. Cross-linking may produce stable solid polymer materials that otherwise would not have the required chemical and physical properties to be utilised. The present inventors have found that the hitherto unwanted dimerisation and tellomerisation, in the radical addition to olefins, provides a means to prepare stable functionalised solid materials.

Compounds such as $(R^5O)_3SiCH_2CH_2Q$ or compounds $(R^5O)_3SiCH(CH_2Q)CH_2CH_2Si(OR^5)_3$ and $(R^5O)_3SiCH_2CH_2Q$ were synthesised via a free radical promoted addition of the corresponding precursor such as an aldehyde, ester or nitrile to vinyl trialkoxy silane. $R^5$ is a linear or branched $C_{1-40}$-alkyl, $C_{2-40}$-alkenyl or $C_{2-40}$-alkynyl group, aryl or $C_{1-40}$-alkylaryl group. The ratio of $(R^5O)_3SiCH_2CH_2Q$ to $(R^5O)_3SiCH(CH_2Q)CH_2CH_2Si(OR^5)_3$ can be controlled through the relevant concentrations of the starting materials trialkoxy vinyl silane to the aldehyde, ester or nitrile. High concentrations of the aldehyde, ester or nitrile to trialkoxy vinyl silane lead to high selectivity for $(R^5O)_3SiCH_2CH_2Q$. Slow addition of the trialkoxy vinyl silane to excess of the aldehyde, ester or nitrile precursor also favours the preparation of $(R^5O)_3SiCH_2CH_2Q$.

For example slow addition of vinyltriethoxy silane to ethyl cyano acetate gave a mixture of $(EtO)_3SiCH_2CH_2CH(CN)CO_2Et$ and $(EtO)_3SiCH(CH_2CH(CN)CO_2Et)CH_2CH_2Si(OEt)_3$. The ratio of these two compounds is dependent on the relative ratio of the starting materials, vinyl triethoxy silane to ethyl cyano acetate. As the ratio of the latter to the former increases then the ratio of the mono to bis trialkoxy silyl compound likewise increases. Using similar reaction conditions $(EtO)_3SiCH_2CH_2CH(C(O)CH_3)CO_2Et$ and $(EtO)_3SiCH(CH_2CH(C(O)CH_3)CO_2Et)CH_2CH_2Si(OEt)_3$ were produced from vinyl triethoxy silane and ethyl acetoacetate. Likewise starting from vinyl triethoxy silane and dimethyl malonate $(EtO)_3SiCH_2CH_2CH(C(O)OCH_3)_2$ and $(EtO)_3SiCH(CH_2CH(C(O)OCH_3)_2)CH_2CH_2Si(OEt)_3$ were produced. From vinyl triethoxy silane and 2,4-pentadione $(EtO)_3SiCH_2CH_2CH(C(O)CH_3)_2$ and $(EtO)_3SiCH(CH_2CH(C(O)CH_3)_2)CH_2CH_2Si(OEt)_3$ were produced.

A wide range of free radical initiators can be used for this reaction and preferred are the peroxides and in particular the alkyl peroxides. Addition of a very small amount of the initiator every few hours improves the overall yield. Reaction temperatures between 60-170° C. can be used, though a reaction temperature of between 100-140° C. is preferred. Di-tert-butyl peroxide is the preferred free radical initiator. Reaction times of between 15 minutes to 48 hours have been used with 6 to 18 hours preferred. On completion the unreacted starting materials are distilled off under reduced pressure and the resultant mixture is heated at between 100-120° C. at 1-2 mm of Hg. The unreacted starting materials can be reused in the next batch.

Acids and bases were used to catalyse the hydrolysis of the silicon esters of $(R^5O)_3SiCH(CH_2Q)CH_2CH_2Si(OR^5)_3$, $(R^5O)_3SiCH_2CH_2Q$ and tetra alkyl orthosilicates to produce the organopolysiloxanes of Formula 1. M. A. Brook in *Silicon in Organic, Organometallic and Polymer Chemistry* Chapter 10, page 318, John Wiley & Sons, Inc., 2000, G. A. Scherer in *Sol-gel science: the physics and chemistry of sol-gel processing*, Boston: Academic Press, 1990, and J. D. Wright in *Sol-gel materials: chemistry and applications*, Amsterdam: Gordon & Breach Science Publishers, 2001 and the references contained within describe sol-gel technology and the hydrolysis of silicon esters.

A range of solvents, known to those skilled in the art of organic chemistry, can be used to conduct this reaction. Alcohols are the preferred solvents particularly methanol and ethanol. After standing for a period of time the solution can be warmed to speed up the formation of the glass. Ratios from 100 to 0.01, by weight, of the alcohol solvent to the combined weight of the reagents can be used, with ranges from 2-10 being preferred. A range of acids may be used to aid hydrolysis with hydrochloric acid in concentrations ranging from 0.1 to 4 M being preferred. Hydrochloric acid, 1 molar, is especially preferred. Ratios, from 0.0001 to 10, of hydrochloric acid, 1 molar, to the combined weight of the reagents are suitably used, with a ratio from 0.01 to 1 being preferred. The reaction mixture may be left to stand at a temperature in the range 0° C.-120° C. to aid hydrolysis and the formation of the Si—O—Si bonds. Temperatures between 20-90° C. are preferred and suitably warming is continued until all the solvent has evaporated and a clear glass is obtained.

Compounds containing A, B, C and D, fragments were prepared through an identical sol gel process using the precursors $(R^5O)_3SiCH_2CH_2Q$, $(R^5O)_3SiCH(CH_2Q)CH_2CH_2Si(OR^5)_3$, $(R^5O)_3SiV$ and tetraalkyl orthosilicate.

In addition to $(R^5O)_3SiCH_2CH_2Q$, $(R^5O)_3SiCH(CH_2Q)CH_2CH_2Si(OR^5)_3$, $(R^5O)_3SiV$ and tetraalkyl orthosilicate, precursors to end groups, cross-linking bridge members or polymer chains such as $R^4SiO_{3/2}$ or $(R^4)_2SiO_{2/2}$ or $TiO_{4/2}$ or $R^4TiO_{3/2}$ or $(R^4)_2TiO_{2/2}$ or $AlO_{3/2}$ or $R^4AlO_{2/2}$, where $R^4$ is as defined above, but is preferably methyl, ethyl or phenyl can be added in varying ratios to produce the desired compound of Formula 1. These end group, cross linking bridge or polymer chain precursors are added at the same time as compounds $(R^5O)_3SiCH_2CH_2Q$, $(R^5O)_3SiCH(CH_2Q)CH_2CH_2Si(OR^5)_3$, $(R^5O)_3SiV$ and tetraalkyl orthosilicate.

Templates to aid the preparation of pores with particular sizes and distributions in compounds of Formula 1 can also be added at this particular stage. On preparation of the solid organopolysiloxanes of Formula 1 these templates can be washed out.

Compounds of Formula 1 can also be prepared by treating a preformed material such as silica or aluminium oxide with $(R^5O)_3SiCH_2CH_2Q$, or with $(R^5O)_3SiCH(CH_2Q)CH_2CH_2Si(OR^5)_3$ and $(R^5O)_3SiCH_2CH_2Q$, or with $(R^5O)_3SiCH_2CH_2Q$, $(R^5O)_3SiCH(CH_2Q)CH_2CH_2Si(OR^5)_3$ and, $(R^5O)_3SiV$ in varying ratios in a solvent.

Compounds of Formula 1 have a wide range of uses. The present invention provides a process for treating a feed material comprising contacting a compound of Formula 1 with a feed material:

i) to effect a chemical reaction by catalytic transformation of a component of the feed material to produce a desired product;

ii) to remove a component of the feed material so as to produce a material depleted in the removed component; or iii) to remove an ionic species in the feed material in an ion exchange process.

The feed material may be a continuous stream for example a continuous process reaction feedstock, or may be in the form of a batch of material for discrete treatment. The feed material, for example a waste water or waste process stream, may be treated to selectively remove a components of the feed. The removed component may be an undesirable material in the feed and the process acts to provide a desired composition for the feed material that has been depleted in the selectively removed component after contact with compounds of Formula 1. This process may be used for example in removing unwanted species from a feed material in a pharmaceutical manufacturing or formulation process to improve the purity level of the pharmaceutical product as regards the removed material, for example metal species.

The process may be employed to remove desired species from a feed material for subsequent processing or analysis, for example a biological molecule such as an enzyme, peptide, protein and nucleic acid may be removed from a feed material to enable further processing or analysis of the removed components.

Compounds of Formula 1 can be used to remove excess reagents and side products from reactions mixtures. The purification of primary, secondary and tertiary amines is a common problem for the fine chemical and pharmaceutical industries. In particular the purification of a secondary amine in the presence of a related primary amine is a common challenge. The carbonyl containing compounds prepared in Examples 2, 4, 5, 7, 9 and 21 can readily remove primary amines and hydrazines from reaction mixtures. In addition these materials can selectively remove primary amines in the presence of secondary and tertiary amines. The following examples illustrate the scavenging of unwanted organic and inorganic compounds by compounds of Formula 1 but are not intended to limit the scope of their capability. Treatment of solutions containing primary amines such as benzylamine, hexylamine and 3-methoxypropylamine with 2 to 4 equivalents of organopolysiloxane ketones of Formula 1 at room temperature for 1 hour led to the complete removal of the amine. With secondary amines such as dibenzylamine no scavenging was observed even with large excesses of organopolysiloxane ketones of Formula 1. Excess borohydrides such as sodium borohydride can be removed on treatment with the organopolysiloxane ketones of Formula 1, such as the products from Examples 2, 4, 5, 16, 18, 19 and 21.

Unlike the polystyrene based scavengers, organopolysiloxane compounds of Formula 1 can work in all solvents, do not suffer from swelling and are not limited in their application to reaction temperatures below 80° C.

Compounds of Formula 1 can also be used for the separation or removal of gases, including the removal of malodorous volatile organic compounds. For example the removal of malodorous amines can be achieved with carboxylic acids prepared in Example 22.

Compounds of Formula 1 can also be used as catalysts and as heterogeneous supports for the immobilisation of catalysts. For example a palladium catalyst formed in Example 24 is an efficient heterogeneous catalyst for carbon bond formation reactions such as Suzuki and Heck, as illustrated in Example 34. These heterogeneous catalysts possess the significant advantages that they can be filtered from the reaction medium and then recycled and reused. This circumvents the problems encountered when homogeneous catalysts are used of significant loss of expensive and often toxic catalysts, catalyst inclusion in the reaction products and the separation of the catalyst from the reaction mixture.

Compounds of Formula 1 can also be used for the removal of cations and anions from water, waste streams, waste waters and potable water. In addition these compounds of Formula 1 can remove impurities such as metal ions contained in chemical products. For example the product of Example 23 can remove main group, transition, lanthanide and actinide metal ions from such environments.

Compounds of Formula 1 can also be used for solid phase synthesis through first attachment of the starting material to the carbonyl group, a number of chemical reactions can then be conducted and in each step purification is facile through simple filtration. At the end of the sequence the desired material is released from the solid phase. In addition compounds of Formula 1 can be used as materials for solid phase extraction where a desired product is purified through selective retention on the functionalised materials whilst the impurities are removed and then it is subsequently released.

Further applications of compounds of Formula 1 include the use as materials for chromatographic separations. For example the materials of Formula 1 can be used in the separation of amines, including optically active amines. Primary amines can be selectively separated from secondary amines using compounds of Formula 1.

Compounds of Formula 1 can be used as materials for gel filtration and high speed size-exclusion chromatography as well as for high pressure liquid chromatography and solid phase extraction.

Compounds of Formula 1 can be used both to immobilise biological molecules such as enzymes, polypeptides, proteins and nucleic acids as well as for their separation and purification. In addition nucleic acids immobilised on compounds of Formula 1 can be used for conducting high volume nucleic acid hybridization assays.

Compounds of Formula 1 can be used as anti-microbial agents. The invention also provides an antimicrobial composition comprising a compound of Formula 1 and a carrier. Compounds of Formula 1 can be applied as thin films onto a variety of surfaces.

The invention will now be described in detail with reference to illustrative examples of the invention.

EXAMPLE 1

A solution containing triethoxyvinylsilane (20.9 g, 0.11 mol) and di-tert butyl peroxide (10 drops) was added dropwise to heptanal (68.71 g, 0.60 mol) at 115° C. under an atmosphere of nitrogen over an hour. The solution was heated to 150° C. maintained at this temperature for 4 h during which di-tert butyl peroxide (10 drops) was added every 20 min. The excess starting material was then removed under reduced pressure at 120° C. to give $(EtO)_3SiCH_2CH_2C(O)C_6H_{13}$ and $(EtO)_3SiCH(CH_2C(O)C_6H_{13})CH_2CH_2Si(OEt)_3$ as a pale yellow oil (32.8 g). $^{13}C$ NMR $CDCl_3$, 210 ppm C=O.

EXAMPLE 2

A mixture of the product from Example 1 (19.76 g) and tetraethyl orthosilicate (84 g) was dissolved in methanol (160 cm$^3$) and 1 M HCl (20 cm$^3$) was added with stirring. The mixture was then left in a water bath at 80° C. until the methanol had evaporated and a glass had formed. The glass was crushed and stirred in refluxing methanol. The material was dried to give a cream coloured powder. IR C=O at 1704 cm$^{-1}$.

EXAMPLE 3

A solution containing triethoxyvinylsilane (20.9 g, 0.11 mol) and di-tert butyl peroxide (10 drops) was added dropwise to heptanal (102.71 g, 0.9 mol) at 115° C. under an atmosphere of nitrogen over two hours. The solution was maintained at this temperature for 22 h during which di-tert butyl peroxide (10 drops) was added every 20 min. The excess starting material was then removed under reduced pressure at 120° C. $(EtO)_3SiCH_2CH_2C(O)C_6H_{13}$ and $(EtO)_3SiCH(CH_2C(O)C_6H_{13})CH_2CH_2Si(OEt)_3$ as a pale yellow oil (31.8 g). $^{13}C$ NMR $CDCl_3$, 210 ppm C=O.

EXAMPLE 4

A mixture of the product from Example 3 (5.76 g) and tetraethyl orthosilicate (32.22 g) was dissolved in methanol (140 cm³) and 1 M HCl (20 cm³) was added with stirring. The mixture was then left in a water bath at 80° C. until the methanol had evaporated and a glass had formed. The glass was crushed and then stirred in refluxing methanol. The material was then dried under reduced pressure of 0.1 mm Hg at 50° C. for 2 h to give a cream coloured powder. IR C=O at 1704 cm$^{-1}$.

EXAMPLE 5

A mixture of the product from Example 1 (4.6 g) and tetraethyl orthosilicate (32.69 g) was dissolved in methanol (140 cm³) and 1 M HCl (18 cm³) was added with stirring. The mixture was then left in a water bath at 80° C. until the methanol had evaporated and a glass had formed. The glass was crushed and then stirred in refluxing methanol. The material was then dried under reduced pressure of 0.1 mm Hg at 50° C. for 2 h to give a cream coloured powder. IR C=O at 1704 cm$^{-1}$.

EXAMPLE 6

A solution containing trimethoxyvinylsilane (16.76 g, 0.11 mol) and di-tert butyl peroxide (10 drops) was added dropwise to octanal (76.93 g, 0.60 mol) at 115° C. under an atmosphere of nitrogen over two hours. The solution was maintained at this temperature for 22 h during which di-tert butyl peroxide (10 drops) was added every 20 min. The excess starting material was then removed under reduced pressure at 120° C. to give (MeO)$_3$SiCH$_2$CH$_2$C(O)C$_7$H$_{15}$ and (MeO)$_3$SiCH(CH$_2$C(O)C$_7$H$_{15}$)CH$_2$CH$_2$Si(OMe)$_3$ a pale yellow oil (37.4 g). $^{13}$C NMR CDC$_3$, 210 ppm C=O.

EXAMPLE 7

A mixture of the product from Example 6 (9.46 g) and tetraethyl orthosilicate (51.67 g) was dissolved in methanol (160 cm³) and 1 M HCl (20 cm³) was added with stirring. The mixture was then left in a water bath at 80° C. until the methanol had evaporated and a glass had formed. The glass was crushed and then stirred in refluxing methanol. The material was then dried under reduced pressure of 0.1 mm Hg at 50° C. for 2 h to give a cream coloured powder. IR C=O at 1704 cm$^{31\ 1}$.

EXAMPLE 8

A solution containing trimethoxyvinylsilane (16.46 g, 0.11 mol) and di-tert butyl peroxide (10 drops) was added dropwise to nonanal (85.34 g, 0.60 mol) at 115° C. under an atmosphere of nitrogen over two hours. The solution was maintained at this temperature for 22 h during which di-tert butyl peroxide (10 drops) was added every 20 min. The excess starting material was then removed under reduced pressure at 120° C. to give (MeO)$_3$SiCH$_2$CH$_2$C(O)C$_8$H$_{17}$ and (MeO)$_3$SiCH(CH$_2$C(O)C$_8$H$_{17}$)CH$_2$CH$_2$Si(OMe)$_3$ as a pale yellow oil (39.2 g). $^{13}$C NMR CDCl$_3$, 210 ppm C=O.

EXAMPLE 9

A solution of the product from Example 8 (6.46 g) and tetraethyl orthosilicate (41.67 g) was dissolved in methanol (160 cm³) and 1 M HCl (20 cm³) was added with stirring. The mixture was then left in a water bath at 80° C. until the methanol had evaporated and a glass had formed. The glass was crushed and then stirred in refluxing methanol. The material was then dried under reduced pressure of 0.1 mm Hg at 50° C. for 2 h to give a cream coloured powder. IR C=O at 1704 cm$^{-1}$.

EXAMPLE 10

A solution of the product from Example 1 (7.1 g) and tetraethyl orthosilicate (41.3 g) and dimethoxy dimethyl silane (2.4 g) was dissolved in methanol (160 cm³) and 1 M HCl (22 cm³) was added with stirring. The mixture was then left in a water bath at 80° C. until the methanol had evaporated and a glass had formed. The glass was crushed and then stirred in refluxing methanol. The material was then dried under reduced pressure of 0.1 mm Hg at 50° C. for 2 h to give a cream coloured powder. IR C=O at 1704 cm$^{-1}$.

EXAMPLE 11

A solution of the product from Example 1 (8.9 g) and tetraethyl orthosilicate (41.3 g) and trimethoxy methyl silane (2.1 g) was dissolved in methanol (160 cm³) and 1 M HCl (21 cm³) was added with stirring. The mixture was then left in a water bath at 80° C. until the methanol had evaporated and a glass had formed. The glass was crushed and then stirred in refluxing methanol. The material was then dried under reduced pressure of 0.1 mm Hg at 50° C. for 2 h to give a cream coloured powder. IR C=O at 1704 cm$^{-1}$.

EXAMPLE 12

A solution of the product from Example 1 (4.9 g) and tetraethyl orthosilicate (41.3 g) and trimethoxy phenyl silane (1.8 g) was dissolved in methanol (160 cm³) and 1 M HCl (21 cm³) was added with stirring. The mixture was then left in a water bath at 80° C. until the methanol had evaporated and a glass had formed. The glass was crushed and then stirred in refluxing methanol. The material was then dried under reduced pressure of 0.1 mm Hg at 50° C. for 2 h to give a cream coloured powder. IR C=O at 1706 cm$^{-1}$.

EXAMPLE 13

A solution containing triethoxyvinylsilane (19.0 g, 0.10 mol), ethyl cyanoacetate (11.3 g, 0.1 mol) and di-tert butyl peroxide (10 drops) was added dropwise to ethyl cyanoacetate (67.8 g, 0.6 mol) at 150° C. under an atmosphere of nitrogen over two hours. The solution was maintained at this temperature for 22 h during which di-tert butyl peroxide (10 drops) was added every 20 min. The excess starting material was then removed under reduced pressure to give ethyl 2-cyano 4-triethoxysilyl butanate and ethyl 2-cyano 4, 6-di(triethoxysilyl) hexanoate as a pale yellow oil (26.8 g).

EXAMPLE 14

A solution of the product from Example 13 (6.83 g) and tetraethyl orthosilicate (53 ml) was dissolved in methanol (160 cm³) and 1 M HCl (28 cm³) was added with stirring. The mixture was then left in a water bath at 80° C. until the methanol had evaporated and a glass had formed. The glass was crushed and then stirred in refluxing methanol. After filtration the material was then dried under reduced pressure of 0.1 mm Hg at 50° C. for 2 h to give a cream coloured powder where in Formula 1 Q is CXYR$^1$ and X=CN, Y=CO$_2$Et, R$^1$=hydrogen, ratio a+b:c=1:0 and d=0.

EXAMPLE 15

A solution containing triethoxyvinylsilane (19.0 g, 0.10 mol), 2,4 pentadione (6.5 g) and di-tert butyl peroxide (10 drops) was added dropwise to 2,4 pentadione (56.5 g, 0.565 mol) at 150° C. under an atmosphere of nitrogen over two hours. The solution was maintained at this temperature for 22 h during which di-tert butyl peroxide (10 drops) was added every 20 min. The excess starting material was then removed under reduced pressure to give 3-acetyl 5-triethoxysilyl pentan-2-one and 3-acetyl 5,7-di(triethoxysilyl) heptan-2-one as a pale yellow oil (25.8 g).

EXAMPLE 16

A solution of the product from Example 15 (6.2 g) and tetraethyl orthosilicate (53 ml) was dissolved in methanol (160 cm$^3$) and 1 M HCl (28 cm$^3$) was added with stirring. The mixture was then left in a water bath at 80° C. until the methanol had evaporated and a glass had formed. The glass was crushed and then stirred in refluxing methanol. After filtration the material was then dried under reduced pressure of 0.1 mm Hg at 50° C. for 2 h to give a cream coloured powder where in Formula 1 Q is CXYR$^1$ and X=C(O)Me, Y=C(O)Me, R$^1$=hydrogen, ratio a+b:c=1:10 and d=0.

EXAMPLE 17

A solution containing triethoxyvinylsilane (22.0 g), ethyl acetoacetate (14.2 g) and di-tert butyl peroxide (3 ml) was added dropwise to 2,4 pentadione (56.5 g, 0.565 mol) at 150° C. under an atmosphere of nitrogen over two hours. The solution was maintained at this temperature for 22 h during which di-tert butyl peroxide (10 drops) was added every 20 min. The excess starting material was removed under reduced pressure to give ethyl 3-acetyl 5-triethoxysilyl butanate and 3-acetyl 5,7 di(triethoxysilyl) hexanate as a pale yellow oil (30.8 g).

EXAMPLE 18

A solution of the product from Example 17 (6.2 g) and tetraethyl orthosilicate (52 ml) was dissolved in methanol (160 cm$^3$) and 1 M HCl (28 cm$^3$) was added with stirring. The mixture was then left in a water bath at 80° C. until the methanol had evaporated and a glass had formed. The glass was crushed and then stirred in refluxing methanol. After filtration the material was then dried under reduced pressure of 0.1 mm Hg at 50° C. for 2 h to give a cream coloured powder where in Formula 1 Q is CXYR$^1$ and X=C(O)Me, Y=C(O)OEt, R$^1$=hydrogen, ratio a+b:c=1:10 and d=0.

EXAMPLE 19

Silica (20 g, 60-200 μm) was added to a solution of the product from Example 17 (6.2 g) in toluene (80 ml) and the resultant mixture was stirred under gentle reflux for 4 h. The solid was filtered and washed well with methanol and dried under reduced pressure to give a cream coloured powder where in Formula 1 Q is CXYR$^1$ and X=C(O)Me, Y=C(O)OEt, R$^1$=hydrogen, ratio a+b:c=1:10 and d=0.

EXAMPLE 20

Silica (20 g, 60-200 μm) was added to a solution of the product from Example 13 (7.2 g) in toluene (80 ml) and the resultant mixture was stirred under gentle reflux for 4 h. The solid was filtered and washed well with methanol and dried under reduced pressure to give a cream coloured powder where in Formula 1 Q is CXYR$^1$ and X=CN, Y=CO$_2$Et, R$^1$=hydrogen, ratio a+b:c=1:10 and d=0.

EXAMPLE 21

Silica (20 g, 60-200 μm) was added to a solution of the product from Example 1 (7.2 g) in toluene (80 ml) and the resultant mixture was stirred under gentle reflux for 4 h. The solid was filtered and washed well with methanol and dried under reduced pressure to give a cream coloured powder where in Formula 1 Q is CXYR$^1$ and X=hydrogen, Y=COC$_6$H$_{13}$, R$^1$=hydrogen, and d=0.

EXAMPLE 22

A mixture containing the product from Example 19 (5 g) and hydrochloric acid (3M, 40 ml) was refluxed with stirring for 4 h and then cooled to room temperature. The solid was filtered and washed well with methanol and dried under reduced pressure to give a cream coloured powder where in Formula 1 Q is CXYR$^1$ and X=C(O)Me, Y=C(O)OH, R$^1$=hydrogen, ratio a+b:c=1:10 and d=0.

EXAMPLE 23

A mixture of the product from Example 22 (1.0 g) in water (30 ml) was treated with an aqueous solution of sodium hydroxide until the pH was 7. The white solid was filtered, washed well with distilled water and finally with methanol. The material was then dried under reduced pressure of 0.1 mm Hg at 80° C. for 2 h to give the sodium carboxylate salt of Example 22 as a white powder (0.9 g).

EXAMPLE 24

A solution of palladium acetate (0.20 g) in THF (50 ml) was added to the sodium salt of the carboxylic acid (Example 23, 2.0 g) and the mixture was stirred overnight. The yellow solid was filtered and washed well with THF and then dried.

EXAMPLE 25

A mixture of anisole (0.03585 g, 0.33 mmol) as a marker, benzylamine (0.04047 g, 0.38 mmol) and the product from Example 2 (0.48685 g, 1.51 mmol) was stirred in CDCl$_3$ (2.5 cm$^3$) at room temperature for 1 h. The mixture was then centrifuged and a $^1$H NMR spectrum of the chloroform solution showed that the benzylamine was completely removed.

EXAMPLE 26

A mixture of anisole (0.02860 g, 0.26 mmol), hexylamine (0.02504 g, 0.25 mmol) and the product from Example 2 (0.32297 g, 1.0 mmol) was stirred in CDCl$_3$ (2.5 cm$^3$) at room temperature for 1 h. The mixture was then centrifuged and a $^1$H NMR spectrum of the chloroform solution showed that the hexylamine was completely removed.

EXAMPLE 27

A mixture of anisole (0.03415 g, 0.32 mmol), 3-methoxypropylamine (0.02901 g, 0.33 mmol) and the product from Example 2 (0.42552 g, 1.32 mmol) was stirred in CDCl$_3$ (2.5 cm$^3$) at room temperature for 1.5 h. The mixture was then centrifuged and a $^1$NMR spectrum of the chloroform solution showed that the 3-methoxypropylamine was completely removed.

EXAMPLE 28

A mixture of dimethoxyethane (0.03580 g, 0.40 mmol) as a marker, dibenzylamine (0.03850 g, 0.19 mmol) and the product from Example 2 (0.25134 g, 0.78 mmol) was stirred in CDCl$_3$ (2.5 cm$^3$) at room temperature for 1 h. The mixture was then centrifuged and a $^1$H NMR spectrum of the chloroform solution showed that the secondary amine dibenzylamine had not been removed.

EXAMPLE 29

A mixture of anisole (0.034 g, 0.32 mmol), hydrazine hydrate (0.015 g, 0.30 mmol) and the product from Example 2 (0.42 g, 1.32 mmol) was stirred in CDCl$_3$ (2.5 cm$^3$) at room temperature for 1.5 h. The mixture was then centrifuged and a $^1$H NMR spectrum of the chloroform solution showed that the hydrazine was completely removed.

EXAMPLE 30

A mixture of dimethoxyethane (0.02304 g, 0.26 mmol), phenylhydrazine (0.03322 g, 0.31 mmol) and the product from Example 2 (0.39570 g, 1.23 mmol) was stirred in CDCl$_3$ (2.5 cm$^3$) at room temperature for 1 h. The mixture was then centrifuged and a $^1$H NMR spectrum of the chloroform solution showed that the phenylhydrazine was completely removed.

EXAMPLE 31

The ketone from Example 2 (2.03 g) was added to a methanolic solution of sodium borohydride (1.19 g) and stirred for 4 h. The mixture was filtered and the solid was washed well with water and then with methanol. IR C=O, peak at 3550 cm$^{-1}$ and no peak at 1702 cm$^{-1}$.

EXAMPLE 32

Hydrazine hydrate was added to a mixture of the ketone from Example 2 (2.23 g) in methanol (15 ml). The mixture was then stirred for 1 h and then filtered. The solid was washed well with methanol and then dried to give the corresponding imine.

EXAMPLE 33

A mixture of the palladium catalyst formed in Example 24 (50 mg), 4-bromotoluene (1.6 mmol), phenyl boronic acid (1.6 mmol) and potassium carbonate (2.4 mmol) in xylene (10 ml) was warmed at 110° C. with stirring for 1 hour. The mixture was filtered and the solid washed with ether. The combined organic extracts were washed with water, dried and then concentrated to give 4-methyl biphenyl in 99% yield. The filtered solid was returned to the reaction flask and further 4-bromotoluene (1.6 mmol), phenyl boronic acid (1.6 mmol) and potassium carbonate (2.4 mmol) in xylene (10 ml) was added and the process repeated to give 4-methyl biphenyl in 99% yield.

EXAMPLE 34

The product from Example 24 (0.2 g) was added to a sample (2 ml) of a solution of ferric (III) chloride (1000 ppm) in water. The mixture was stirred for 1 h at room temperature and then filtered. Analysis of the filtrate showed that ferric chloride had been removed.

The invention claimed is:

1. A compound of Formula 1:

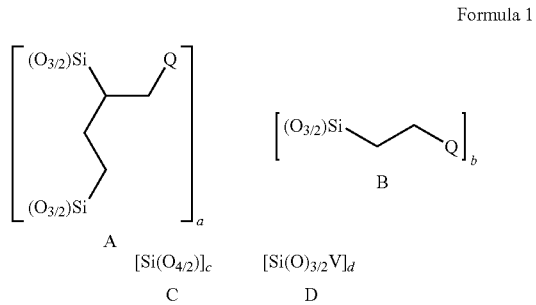

Formula 1 wherein Q is selected from CXYR$^1$ and —C(Z)R wherein Z is divalent and selected from oxygen, NR$^2$ and NNR$^2$R$^3$ or comprises OH and H, and wherein X and Y are each selected from hydrogen, —C(Z)R, CN and C(O)W and W is selected from OH, OR$^6$, O(M$^{+n}$)$_{1/n}$ and NR$^2$R$^3$ and R, R$^1$, R$^2$, R$^3$ and R$^6$ are each selected from hydrogen and an optionally substituted linear or branched group selected from C$_{1-40}$-alkyl, C$_{2-40}$-alkenyl, C$_{2-40}$-alkynyl group, an aryl and C$_{1-40}$-alkylaryl group and M is a metal ion selected from a lanthanide, actinide, main group or transition metal and V is selected from an optionally substituted linear or branched group selected from C$_{1-40}$-alkyl, C$_{2-40}$-alkenyl, C$_{2-40}$-alkynyl group, an aryl group, a C$_{1-40}$-alkylaryl, sulfide, sulfoxide, sulfone, amine, a polyalkyl amine, a phosphine or other phosphorous containing group; n is an integer from 1 to 4;

the free valences of the silicate oxygen atoms are saturated by one or more of:

silicon atoms of other groups of Formula 1, hydrogen, a linear or branched C$_{1-12}$-alkyl group, by end groups R$^4_3$M$^1$O$_{1/2}$, by cross-linking bridge members R$^4_q$M$^1$(OR$^5$)$_m$O$_{k/2}$, Al(OR$^5$)$_{3-p}$O$_{p/2}$ or R$^4$Al(OR$^5$)$_{2-r}$O$_{r/2}$ or by chains comprising (R$^4_e$SiO$_{f/2}$)$_g$;

where M$^1$ is Si or Ti;

e is an integer from 2 to 3 and f is an integer from 1 to 2 such that e+f=4 and g is an integer from 1 to 10$^8$;

R$^5$ is a linear or branched C$_{1-40}$, alkyl group, an aryl or C$_{1-40}$-alkylaryl group; and R$^4$ is a linear or branched C$_{1-40}$-alkyl group, an aryl or C$_{1-40}$-alkylaryl group;

k is an integer from 1 to 3 and q and m are integers from 0 to 2, such that m+k+q=4;

p is an integer from 1 to 3; and r is an integer from 1 to 2;

wherein both B and C are always present and a, b, c and d are integers such that the molar ratio of b:a+c+d, is from 0.00001 to 100,000, and wherein CXYR$^1$ and —C(Z)R are monovalent and connected to the rest of the compound through the carbon atom, and wherein A, B, C, and D designate the four components of the compound of Formula 1.

2. The compound as claimed in claim 1 which is selected from one or more end groups, cross linking bridge members or polymer chains and wherein the molar ratio of end group, cross linker and/or chain to a+b+c+d is from 0.001 to 999:1.

3. The compound as claimed in claim 1 that is selected from an end group selected from a trialkyl or triaryl alkoxysilane, or a cross linking bridge member derived from an orthosilicate, a titanium alkoxide or a aluminium trialkoxide or a polymer chain selected from a mono alkyl or mono aryl trialkoxysilane or a di alkyl or di aryl dialkoxysilane.

4. The compound as claimed in claim 3 wherein the one or more end groups or cross-linking bridges or polymer chains are selected from $R^4_3SiO_{1/2}$, $R^4_2SiO_{2/2}$, $TiO_{4/2}$, $R^4TiO_{3/2}$, $R^4_2TiO_{2/2}$, $AlO_{3/2}$ and $R^4AlO_{2/2}$.

5. The compound as claimed in claim 4 wherein $R^4$ is a $C_{1-4}$-alkyl, $C_{2-12}$-alkenyl or aryl group.

6. The compound as claimed in claim 1 wherein Z is divalent and selected from oxygen, $NR^2$ and $NNR^2R^3$ or comprises OH and H, and R, where —C(Z)R is present, and $R^1$, where $CXYR^1$ is present, are each selected from an optionally substituted $C_{1-20}$-alkyl, $C_{2-12}$-alkenyl, $C_{2-12}$-alkynyl, aryl, $C_{1-8}$-alkylaryl group and $R^2$, $R^3$ and $R^6$ are each selected from an optionally substituted $C_{1-12}$-alkyl, $C_{2-12}$-alkenyl, $C_{2-12}$-alkynyl, aryl and $C_{1-8}$-alkylaryl group and V is selected from an optionally substituted linear or branched $C_{1-20}$-alkyl, $C_{2-20}$-alkenyl, $C_{2-20}$-alkynyl group, an aryl group and a $C_{1-20}$-alkylaryl group, sulfide, sulfoxide, sulfone, amine, a polyalkyl amine, phosphine or other phosphorous containing group.

7. The compound as claimed in claim 6 wherein Z is divalent and selected from oxygen, $NR^2$ and $NNR^2R^3$ or comprises OH and H, W is selected from OH, $OR^6$, $O(M^{+n})_{1/n}$ and $NR^2R^3$ and R and $R^1$ are each selected from an optionally substituted $C_{1-20}$-alkyl, $C_{2-12}$-alkenyl, $C_{2-12}$-alkynyl, aryl $C_{1-8}$-alkylaryl group and $R^2$, $R^3$ and $R^6$ are each selected from $C_{1-4}$-alkyl, $C_{2-6}$-alkenyl, $C_{2-6}$-alkynyl, aryl and $C_{1-8}$-alkylaryl and V is selected from an optionally substituted linear or branched $C_{1-6}$-alkyl, $C_{2-6}$-alkenyl and $C_{2-6}$-alkynyl group and an aryl group.

8. The compound as claimed in claim 1 wherein Q is $CXYR^1$ wherein X and Y are each selected from hydrogen, —C(O)R, CN or C(O)W and W is selected from OH, $OR^6$, $O(M^{+n})_{1/n}$, R and $R^1$ are, independently, an optionally substituted $C_{1-8}$-alkyl group, $R^6$ is a $C_{1-4}$-alkyl group
and M is a metal ion selected from a lanthanide, main group or transition metal and V is vinyl, $C_{1-4}$-alkyl, phenyl or a $C_{1-8}$-alkylaryl group.

9. A compound of formula $(R^5O)_3SiCH_2CH_2Q$ wherein Q is selected from $CXYR^1$ and —C(Z)R wherein Z is divalent and selected from oxygen, $NR^2$ and $NNR^2R^3$ or comprises OH and H, and wherein X and Y are each selected from —C(Z)R, CN and C(O)W and W is selected from OH, $OR^6$, $O(M^{+n})_{1/n}$ and $NR^2R^3$ and R, $R^1$, $R^2$, $R^3$ and $R^6$ are each selected from hydrogen and an optionally substituted linear or branched group selected from $C_{1-40}$-alkyl, $C_{2-40}$-alkenyl, $C_{2-40}$-alkynyl group, an aryl and $C_{1-40}$-alkylaryl group and M is a metal ion selected from a lanthanide, actinide, main group or transition metal; n is an integer from 1 to 4
and $R^5$ is a linear or branched $C_{1-40}$, alkyl group, an aryl or $C_{1-40}$-alkylaryl group.

10. A compound of formula $(R^5O)_3SiCH(CH_2Q)CH_2CH_2Si(OR^5)_3$ wherein Q is selected from $CXYR^1$ and —C(Z)R wherein Z is divalent and selected from oxygen, $NR^2$ and $NNR^2R^3$ or comprises OH and H, and wherein X and Y are each selected from —C(Z)R, CN and C(O)W and W is selected from OH, $OR^6$, $O(M^{+n})_{1/n}$ and $NR^2R^3$ and R, $R^1$, $R^2$, $R^3$ and $R^6$ are each selected from hydrogen and an optionally substituted linear or branched group selected from $C_{1-40}$-alkyl, $C_{2-40}$-alkenyl, $C_{2-40}$-alkynyl group, an aryl and $C_{1-40}$-alkylaryl group and M is a metal ion selected from a lanthanide, actinide, main group or transition metal; n is an integer from 1 to 4.

11. A process for the preparation of a compound as claimed in claim 9, the process comprising the free radical addition of $CHXYR^1$ to trialkoxy vinyl $H_2C=CHSi(OR^5)_3$, where $R^5$ is a linear or branched $C_{1-12}$ alkyl, aryl or alkylaryl group; in the presence of a free radical initiator.

12. A process for the preparation of a compound as claimed in claim 1, the process comprising the treatment of silica or alumina with a compound of formula $(R^5O)_3SiCH_2CH_2Q$, and $(R^5O)_3SiCH(CH_2Q)CH_2CH_2Si(OR^5)_3$ and $(R^{50})_3SiV$ in a solvent.

13. A process for treating a feedstock of a carbon-carbon bond formation reaction, an oxidation, reduction, alkylation, polymerisation, hydroformylation, arylation, acylation, isomerisation, carboxylation, carbonylation, esterification, trans-esterification or rearrangement reaction, the process comprising catalyzing the reaction by using a compound of Formula 1:

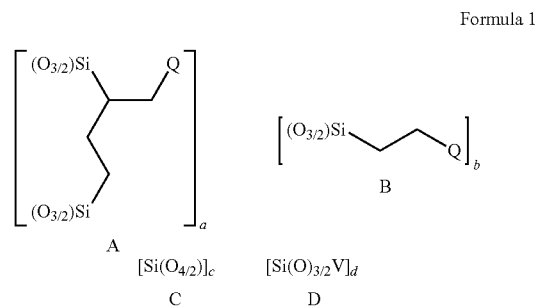

Formula 1 wherein Q is selected from $CXYR^1$ and —C(Z)R wherein Z is divalent and selected from oxygen, $NR^2$ and $NNR^2R^3$ or comprises OH and H, and wherein X and Y are each selected from hydrogen, —C(Z)R, CN and C(O)W and W is selected from OH, $OR^6$, $O(M^{+n})_{1/n}$ and $NR^2R^3$ and R, $R^1$, $R^2$, $R^3$ and $R^6$ are each selected from hydrogen and an optionally substituted linear or branched group selected from $C_{1-40}$-alkyl, $C_{2-40}$-alkenyl, $C_{2-40}$-alkynyl group, an aryl and $C_{1-40}$-alkylaryl group and M is a metal ion selected from a lanthanide, actinide, main group or transition metal and V is selected from an optionally substituted linear or branched group selected from $C_{1-40}$-alkyl, $C_{2-40}$-alkenyl, $C_{2-40}$-alkynyl group, an aryl group, a $C_{1-40}$-alkylaryl, sulfide, sulfoxide, sulfone, amine, a polyalkyl amine, a phosphine or other phosphorous containing group; n is an integer from 1 to 4;
the free valences of the silicate oxygen atoms are saturated by one or more of:
silicon atoms of other groups of Formula 1, hydrogen, a linear or branched $C_{1-12}$-alkyl group, by end groups $R^4_3M^1O_{1/2}$, by cross-linking bridge members $R^4_qM^1(OR^5)_mO_{k/2}$, $Al(OR^5)_{3-p}O_{p/2}$ or $R^4Al(OR^5)_{2-r}O_{r/2}$ or by chains comprising $(R^4_eSiO_{f/2})_g$;
where $M^1$ is Si or Ti;
e is an integer from 2 to 3 and f is an integer from 1 to 2 such that e+f=4 and g is an integer from 1 to $10^8$;
$R^5$ is a linear or branched $C_{1-40}$, alkyl group, an aryl or $C_{1-40}$-alkylaryl group; and $R^4$ is a linear or branched $C_{1-40}$-alkyl group, an aryl or $C_{1-40}$-alkylaryl group;
k is an integer from 1 to 3 and q and m are integers from 0 to 2;
such that m+k+q=4;
p is an integer from 1 to 3; and r is an integer from 1 to 2;
wherein both B and C are always present and a, b, c and d are integers such that the molar ratio of b:a+c+d, is from 0.00001 to 100,000, and wherein CXYR¹ and —C(Z)R are monovalent and connected to the rest of the compound through the carbon atom, and wherein A, B, C, and D designate the four components of the compound of Formula 1.

14. A process for the removal of or reducing the level of an unwanted organic or inorganic compound from a liquid substrate, the process comprising contacting said substrate with a compound of Formula 1:

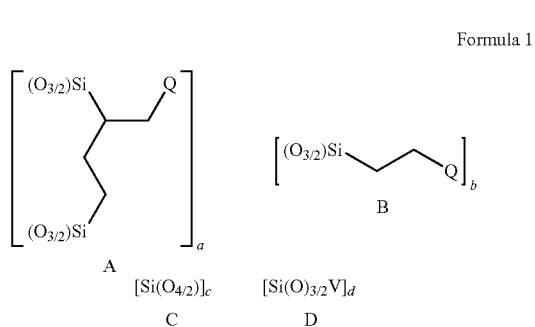

Formula 1 wherein Q is selected from CXYR¹ and —C(Z)R wherein Z is divalent and selected from oxygen, $NR^2$ and $NNR^2R^3$ or comprises OH and H, and wherein X and Y are each selected from hydrogen, —C(Z)R, CN and C(O)W and W is selected from OH, $OR^6$, $O(M^{+n})_{1/n}$ and $NR^2R^3$ and R, $R^1$, $R^2$, $R^3$ and $R^6$ are each selected from hydrogen and an optionally substituted linear or branched group selected from $C_{1-40}$-alkyl, $C_{2-40}$-alkenyl, $C_{2-40}$-alkynyl group, an aryl and $C_{1-40}$-alkylaryl group and M is a metal ion selected from a lanthanide, actinide, main group or transition metal and V is selected from an optionally substituted linear or branched group selected from $C_{1-40}$-alkyl, $C_{2-40}$-alkenyl, $C_{2-40}$-alkynyl group, an aryl group, a $C_{1-40}$-alkylaryl, sulfide, sulfoxide, sulfone, amine, a polyalkyl amine, a phosphine or other phosphorous containing group; n is an integer from 1 to 4;

the free valences of the silicate oxygen atoms are saturated by one or more of:

silicon atoms of other groups of Formula 1, hydrogen, a linear or branched $C_{1-12}$-alkyl group, by end groups $R^4_3M^1O_{1/2}$, by cross-linking bridge members $R^4_qM^1(OR^5)_mO_{k/2}$, $Al(OR^5)_{3-p}O_{p/2}$ or $R^4Al(OR^5)_{2-r}O_{r/2}$ or by chains comprising $(R^4_eSiO_{f/2})_g$;

where $M^1$ is Si or Ti;

e is an integer from 2 to 3 and f is an integer from 1 to 2 such that e+f=4 and g is an integer from 1 to $10^8$;

$R^5$ is a linear or branched $C_{1-40}$, alkyl group, an aryl or $C_{1-40}$-alkylaryl group; and $R^4$ is a linear or branched $C_{1-40}$-alkyl group, an aryl or $C_{1-40}$-alkylaryl group;

k is an integer from 1 to 3 and q and m are integers from 0 to 2;

such that m+k+q=4;

p is an integer from 1 to 3; and r is an integer from 1 to 2;

wherein both B and C are always present and a, b, c and d are integers such that the molar ratio of b:a+c+d, is from 0.00001 to 100,000, and wherein CXYR¹ and —C(Z)R are monovalent and connected to the rest of the compound through the carbon atom, and wherein A, B, C, and D designate the four components of the compound of Formula 1.

15. The process according to claim 14 in which the unwanted compound is removed from a reaction mixture, waste stream or waste water or bound or attached to other organic compounds.

16. A process of acid-catalysing a chemical reaction, the process comprising contacting a feedstock to be subjected to acid catalysis with a compound of Formula 1:

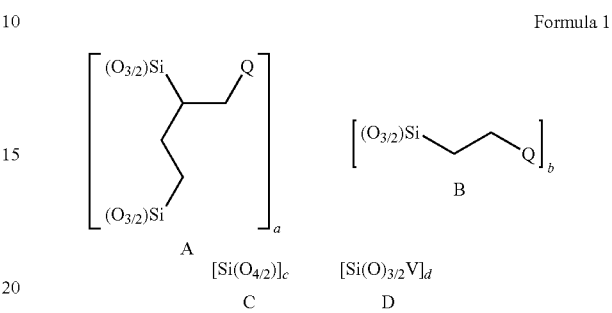

Formula 1 wherein Q is selected from CXYR¹ and —C(Z)R wherein Z is divalent and selected from oxygen, $NR^2$ and $NNR^2R^3$ or comprises OH and H, and wherein X and Y are each selected from hydrogen, —C(Z)R, CN and C(O)W and W is selected from OH, $OR^6$, $O(M^{+n})_{1/n}$ and $NR^2R^3$ and R, $R^1$, $R^2$, $R^3$ and $R^6$ are each selected from hydrogen and an optionally substituted linear or branched group selected from $C_{1-40}$-alkyl, $C_{2-40}$-alkenyl, $C_{2-40}$-alkynyl group, an aryl and $C_{1-40}$-alkylaryl group and M is a metal ion selected from a lanthanide, actinide, main group or transition metal and V is selected from an optionally substituted linear or branched group selected from $C_{1-40}$-alkyl, $C_{2-40}$-alkenyl, $C_{2-40}$-alkynyl group, an aryl group, a $C_{1-40}$-alkylaryl, sulfide, sulfoxide, sulfone, amine, a polyalkyl amine, a phosphine or other phosphorous containing group; n is an integer from 1 to 4;

the free valences of the silicate oxygen atoms are saturated by one or more of:

silicon atoms of other groups of Formula 1, hydrogen, a linear or branched $C_{1-12}$-alkyl group, by end groups $R^4_3M^1O_{1/2}$, by cross-linking bridge members $R^4_qM^1(OR^5)_mO_{k/2}$, $Al(OR^5)_{3-p}O_{p/2}$ or $R^4Al(OR^5)_{2-r}O_{r/2}$ or by chains comprising $(R^4_eSiO_{f/2})_g$;

where $M^1$ is Si or Ti;

e is an integer from 2 to 3 and f is an integer from 1 to 2 such that e+f=4 and g is an integer from 1 to $10^8$;

$R^5$ is a linear or branched $C_{1-40}$, alkyl group, an aryl or $C_{1-40}$-alkylaryl group; and $R^4$ is a linear or branched $C_{1-40}$-alkyl group, an aryl or $C_{1-40}$-alkylaryl group;

k is an integer from 1 to 3 and q and m are integers from 0 to 2;

such that m+k+q=4;

p is an integer from 1 to 3; and r is an integer from 1 to 2;

wherein both B and C are always present and a, b, c and d are integers such that the molar ratio of b:a+c+d, is from 0.00001 to 100,000, and wherein CXYR¹ and —C(Z)R are monovalent and connected to the rest of the compound through the carbon atom, and wherein A, B, C, and D designate the four components of the compound of Formula 1.

17. A process of carrying out a heterogeneously-catalysed reaction selected from oxidation, reduction, a carbon-carbon bond formation reaction, alkylation, polymerisation, hydroformylation, arylation, acylation, isomerisation, carboxylation, carbonylation, esterification, trans-esterification or rearrangement reaction on a feedstock to be subjected to the said reaction, the process comprising catalyzing the reaction by using a compound of Formula 1:

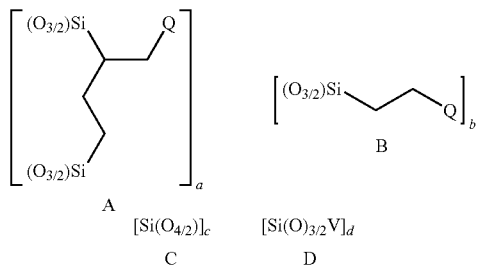

Formula 1 wherein Q is selected from $CXYR^1$ and —C(Z)R wherein Z is divalent and selected from oxygen, $NR^2$ and $NNR^2R^3$ or comprises OH and H, and wherein X and Y are each selected from hydrogen, —C(Z)R, CN and C(O)W and W is selected from OH, $OR^6$, $O(M^{+n})_{1/n}$ and $NR^2R^3$ and R, $R^1$, $R^2$, $R^3$ and $R^6$ are each selected from hydrogen and an optionally substituted linear or branched group selected from $C_{1-40}$-alkyl, $C_{2-40}$-alkenyl, $C_{2-40}$-alkynyl group, an aryl and $C_{1-40}$-alkylaryl group and M is a metal ion selected from a lanthanide, actinide, main group or transition metal and V is selected from an optionally substituted linear or branched group selected from $C_{1-40}$-alkyl, $C_{2-40}$-alkenyl, $C_{2-40}$-alkynyl group, an aryl group, a $C_{1-40}$-alkylaryl, sulfide, sulfoxide, sulfone, amine, a polyalkyl amine, a phosphine or other phosphorous containing group; n is an integer from 1 to 4;

the free valences of the silicate oxygen atoms are saturated by one or more of:

silicon atoms of other groups of Formula 1, hydrogen, a linear or branched $C_{1-12}$-alkyl group, by end groups $R^4_3M^1O_{1/2}$, by cross-linking bridge members $R^4_qM^1(OR^5)_mO_{k/2}$, $Al(OR^5)_{3-p}O_{p/2}$ or $R^4Al(OR^5)_{2-r}O_{r/2}$ or by chains comprising $(R^4_eSiO_{f/2})_g$;

where $M^1$ is Si or Ti;

e is an integer from 2 to 3 and f is an integer from 1 to 2 such that e+f=4 and g is an integer from 1 to $10^8$;

$R^5$ is a linear or branched $C_{1-40}$, alkyl group, an aryl or $C_{1-40}$-alkylaryl group; and $R^4$ is a linear or branched $C_{1-40}$-alkyl group, an aryl or $C_{1-40}$-alkylaryl group;

k is an integer from 1 to 3 and q and m are integers from 0 to 2;

such that m+k+q=4;

p is an integer from 1 to 3; and r is an integer from 1 to 2;

wherein both B and C are always present and a, b, c and d are integers such that the molar ratio of b:a+c+d, is from 0.00001 to 100,000, and wherein $CXYR^1$ and —C(Z)R are monovalent and connected to the rest of the compound through the carbon atom, and wherein A, B, C, and D designate the four components of the compound of Formula 1.

18. A process of carrying out a cation or anion exchange reaction with a substrate containing ions to be exchanged, the process comprising using in the process a compound of Formula 1:

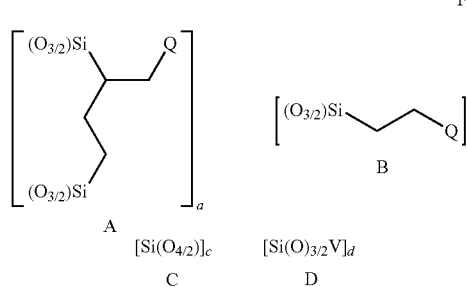

Formula 1 wherein Q is selected from $CXYR^1$ and —C(Z)R wherein Z is divalent and selected from oxygen, $NR^2$ and $NNR^2R^3$ or comprises OH and H, and wherein X and Y are each selected from hydrogen, —C(Z)R, CN and C(O)W and W is selected from OH, $OR^6$, $O(M^{+n})_{1/n}$ and $NR^2R^3$ and R, $R^1$, $R^2$, $R^3$ and $R^6$ are each selected from hydrogen and an optionally substituted linear or branched group selected from $C_{1-40}$-alkyl, $C_{2-40}$-alkenyl, $C_{2-40}$-alkynyl group, an aryl and $C_{1-40}$-alkylaryl group and M is a metal ion selected from a lanthanide, actinide, main group or transition metal and V is selected from an optionally substituted linear or branched group selected from $C_{1-40}$-alkyl, $C_{2-40}$-alkenyl, $C_{2-40}$-alkynyl group, an aryl group, a $C_{1-40}$-alkylaryl, sulfide, sulfoxide, sulfone, amine, a polyalkyl amine, a phosphine or other phosphorous containing group; n is an integer from 1 to 4;

the free valences of the silicate oxygen atoms are saturated by one or more of:

silicon atoms of other groups of Formula 1, hydrogen, a linear or branched $C_{1-12}$-alkyl group, by end groups $R^4_3M^1O_{1/2}$, by cross-linking bridge members $R^4_qM^1(OR^5)_mO_{k/2}$, $Al(OR^5)_{3-p}O_{p/2}$ or $R^4Al(OR^5)_{2-r}O_{r/2}$ or by chains comprising $(R^4_eSiO_{f/2})_g$;

where $M^1$ is Si or Ti;

e is an integer from 2 to 3 and f is an integer from 1 to 2 such that e+f=4 and g is an integer from 1 to $10^8$;

$R^5$ is a linear or branched $C_{1-40}$, alkyl group, an aryl or $C_{1-40}$-alkylaryl group; and $R^4$ is a linear or branched $C_{1-40}$-alkyl group, an aryl or $C_{1-40}$-alkylaryl group;

k is an integer from 1 to 3 and q and m are integers from 0 to 2;

such that m+k+q=4;

p is an integer from 1 to 3; and r is an integer from 1 to 2;

wherein both B and C are always present and a, b, c and d are integers such that the molar ratio of b:a+c+d, is from 0.00001 to 100,000, and wherein $CXYR^1$ and —C(Z)R are monovalent and connected to the rest of the compound through the carbon atom, and wherein A, B, C, and D designate the four components of the compound of Formula 1 with the substrate.

19. A process for immobilising a biological molecule, the process comprising contacting said biological molecule with a compound of Formula 1:

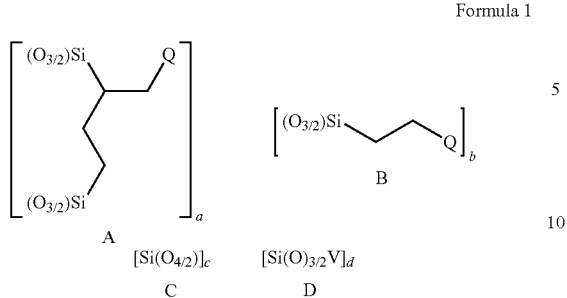

Formula 1

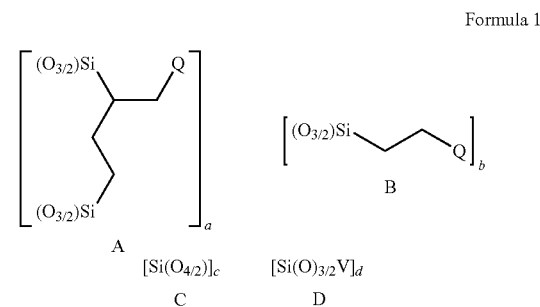

Formula 1 wherein Q is selected from $CXYR^1$ and —C(Z)R wherein Z is divalent and selected from oxygen, $NR^2$ and $NNR^2R^3$ or comprises OH and H, and wherein X and Y are each selected from hydrogen, —C(Z)R, CN and C(O)W and W is selected from OH, $OR^6$, $O(M^{+n})_{1/n}$ and $NR^2R^3$ and R, $R^1$, $R^2$, $R^3$ and $R^6$ are each selected from hydrogen and an optionally substituted linear or branched group selected from $C_{1-40}$-alkyl, $C_{2-40}$-alkenyl, $C_{2-40}$-alkynyl group, an aryl and $C_{1-40}$-alkylaryl group and M is a metal ion selected from a lanthanide, actinide, main group or transition metal and V is selected from an optionally substituted linear or branched group selected from $C_{1-40}$-alkyl, $C_{2-40}$-alkenyl, $C_{2-40}$-alkynyl group, an aryl group, a $C_{1-40}$-alkylaryl, sulfide, sulfoxide, sulfone, amine, a polyalkyl amine, a phosphine or other phosphorous containing group; n is an integer from 1 to 4;

the free valences of the silicate oxygen atoms are saturated by one or more of:

silicon atoms of other groups of Formula 1, hydrogen, a linear or branched $C_{1-12}$-alkyl group, by end groups $R^4_3M^1O_{1/2}$, by cross-linking bridge members $R^4_qM^1(OR^5)_mO_{k/2}$, $Al(OR^5)_{3-p}O_{p/2}$ or $R^4Al(OR^5)_{2-r}O_{r/2}$ or by chains comprising $(R^4_eSiO_{f/2})_g$;

where $M^1$ is Si or Ti;

e is an integer from 2 to 3 and f is an integer from 1 to 2 such that e+f=4 and g is an integer from 1 to $10^8$;

$R^5$ is a linear or branched $C_{1-40}$, alkyl group, an aryl or $C_{1-40}$-alkylaryl group; and $R^4$ is a linear or branched $C_{1-40}$-alkyl group, an aryl or $C_{1-40}$-alkylaryl group;

k is an integer from 1 to 3 and q and m are integers from 0 to 2;

such that m+k+q=4;

p is an integer from 1 to 3; and r is an integer from 1 to 2;

wherein both B and C are always present and a, b, c and d are integers such that the molar ratio of b:a+c+d, is from 0.00001 to 100,000, and wherein $CXYR^1$ and —C(Z)R are monovalent and connected to the rest of the compound through the carbon atom, and wherein A, B, C, and D designate the four components of the compound of Formula 1.

20. An anti-microbial composition comprising a compound of Formula 1:

wherein Q is selected from $CXYR^1$ and —C(Z)R wherein Z is divalent and selected from oxygen, $NR^2$ and $NNR^2R^3$ or comprises OH and H, and wherein X and Y are each selected from hydrogen, —C(Z)R, CN and C(O)W and W is selected from OH, $OR^6$, $O(M^{+n})_{1/n}$ and $NR^2R^3$ and R, $R^1$, $R^2$, $R^3$ and $R^6$ are each selected from hydrogen and an optionally substituted linear or branched group selected from $C_{1-40}$-alkyl, $C_{2-40}$-alkenyl, $C_{2-40}$-alkynyl group, an aryl and $C_{1-40}$-alkylaryl group and M is a metal ion selected from a lanthanide, actinide, main group or transition metal and V is selected from an optionally substituted linear or branched group selected from $C_{1-40}$-alkyl, $C_{2-40}$-alkenyl, $C_{2-40}$-alkynyl group, an aryl group, a $C_{1-40}$-alkylaryl, sulfide, sulfoxide, sulfone, amine, a polyalkyl amine, a phosphine or other phosphorous containing group; n is an integer from 1 to 4;

the free valences of the silicate oxygen atoms are saturated by one or more of:

silicon atoms of other groups of Formula 1, hydrogen, a linear or branched $C_{1-12}$-alkyl group, by end groups $R^4_3M^1O_{1/2}$, by cross-linking bridge members $R^4_qM^1(OR^5)_mO_{k/2}$, $Al(OR^5)_{3-p}O_{p/2}$ or $R^4Al(OR^5)_{2-r}O_{r/2}$ or by chains comprising $(R^4_eSiO_{f/2})_g$;

where $M^1$ is Si or Ti;

e is an integer from 2 to 3 and f is an integer from 1 to 2 such that e+f=4 and g is an integer from 1 to $10^8$;

$R^5$ is a linear or branched $C_{1-40}$, alkyl group, an aryl or $C_{1-40}$-alkylaryl group; and $R^4$ is a linear or branched $C_{1-40}$-alkyl group, an aryl or $C_{1-40}$-alkylaryl group;

k is an integer from 1 to 3 and q and m are integers from 0 to 2;

such that m+k+q=4;

p is an integer from 1 to 3; and r is an integer from 1 to 2;

wherein both B and C are always present and a, b, c and d are integers such that the molar ratio of b:a+c+d, is from 0.00001 to 100,000, and wherein $CXYR^1$ and —C(Z)R are monovalent and connected to the rest of the compound through the carbon atom, and wherein A, B, C, and D designate the four components of the compound of Formula 1 and a carrier.

21. The process for the preparation of a compound as claimed in claim 10, the process comprising the free radical addition of $CHXYR^1$ to trialkoxy vinyl silane, $H_2C$=$CHSi(OR^5)_3$, where $R^5$ is a linear or branched $C_{1-12}$ alkyl, aryl or alkylaryl group; in the presence of a free radical initiator.

* * * * *